(12) United States Patent
Mohan et al.

(10) Patent No.: US 7,686,803 B2
(45) Date of Patent: Mar. 30, 2010

(54) ABLATION PROBE WITH STABILIZING MEMBER

(75) Inventors: Ashik A. Mohan, Petaluma, CA (US);
William K. Wheeler, Alamo, CA (US);
Eric K. Y. Chan, San Carlos, CA (US);
Bhupinder S. Minhas, Brentwood, CA (US)

(73) Assignee: Cardima, Inc., Fremont, CA (US)

( * ) Notice: Subject to any disclaimer, the term of this patent is extended or adjusted under 35 U.S.C. 154(b) by 1256 days.

(21) Appl. No.: 11/128,577

(22) Filed: May 14, 2005

(65) Prior Publication Data

US 2006/0025762 A1 Feb. 2, 2006

Related U.S. Application Data

(60) Provisional application No. 60/571,081, filed on May 14, 2004, provisional application No. 60/602,415, filed on Aug. 18, 2004, provisional application No. 60/614,703, filed on Sep. 30, 2004.

(51) Int. Cl.
*A61B 18/14* (2006.01)
(52) U.S. Cl. ........................................................ 606/41
(58) Field of Classification Search .................... 606/41
See application file for complete search history.

(56) References Cited

U.S. PATENT DOCUMENTS 6,663,622 B1 12/2003 Foley et al.

| | | | |
|---|---|---|---|
| 2002/0002372 A1 | 1/2002 | Jahns et al. | |
| 2003/0120268 A1 | 6/2003 | Bertolero et al. | |
| 2004/0054363 A1 | 3/2004 | Vaska et al. | |
| 2004/0186467 A1* | 9/2004 | Swanson et al. | .............. 606/41 |

FOREIGN PATENT DOCUMENTS

| WO | WO 97/10753 | 3/1997 |
|---|---|---|
| WO | WO 2004/093698 | 11/2004 |

OTHER PUBLICATIONS

International Search Report for PCT/US2005/016715 mailed Sep. 6, 2005.
Written Opinion Of The International Searching Authority for PCT/US2005/016715 mailed Sep. 6, 2005.

* cited by examiner

*Primary Examiner*—Lee S Cohen
(74) *Attorney, Agent, or Firm*—Edward J. Lynch

(57) ABSTRACT

A surgical ablation probe assembly particularly suitable for ablating tissue on a surface of a patient's heart having an ablation member and a stabilizing member for guiding the probe assembly to an intracorporeal location such as a surface of the patient's heart. The elongated ablation member generally has at least one ablation electrode on a distal shaft section. The stabilizing member has a vacuum lumen which applies a vacuum to the inner chamber of the stabilizing member to aspirate fluid from within the chamber or about the stabilizing member and can aid in holding the stabilizing member to an intracorporeal surface such as the epicardial or endocardial surface of the patient's heart. The probe assembly may also have a removable stylet to help retain the shape of the distal portion. The assembly is suitable for treating a patient for atrial arrhythmia, by forming linear or curvilinear lesions and preferably a continuous lesion on the surface of the patient's heart.

11 Claims, 17 Drawing Sheets

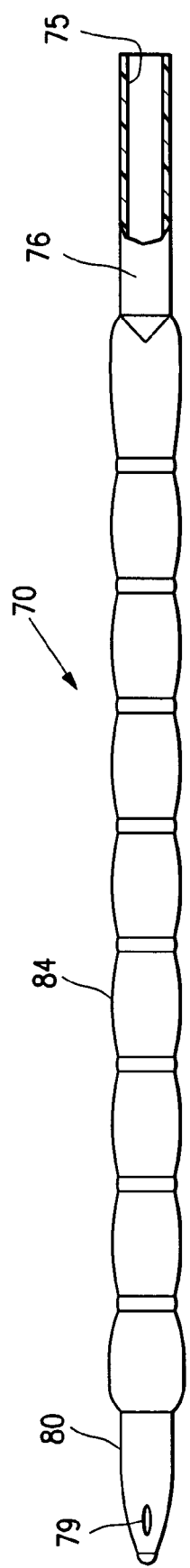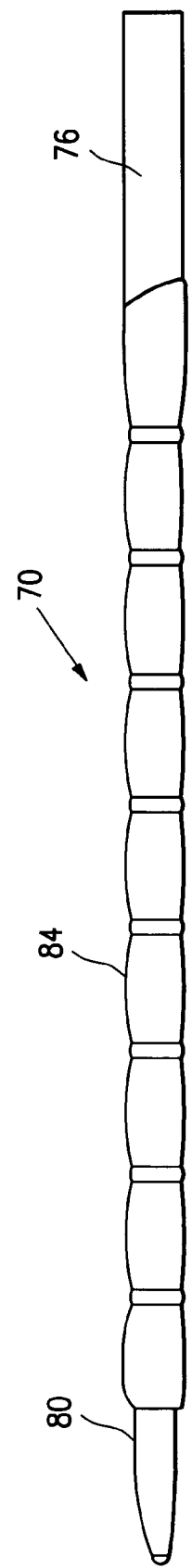
FIG. 11
FIG. 12

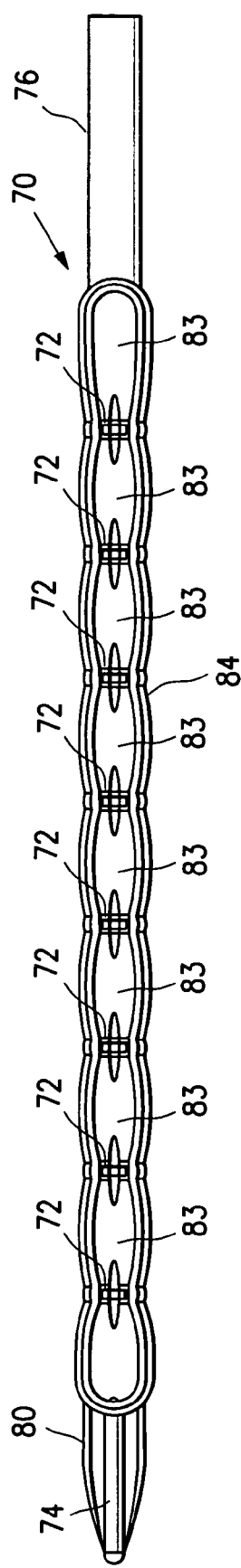
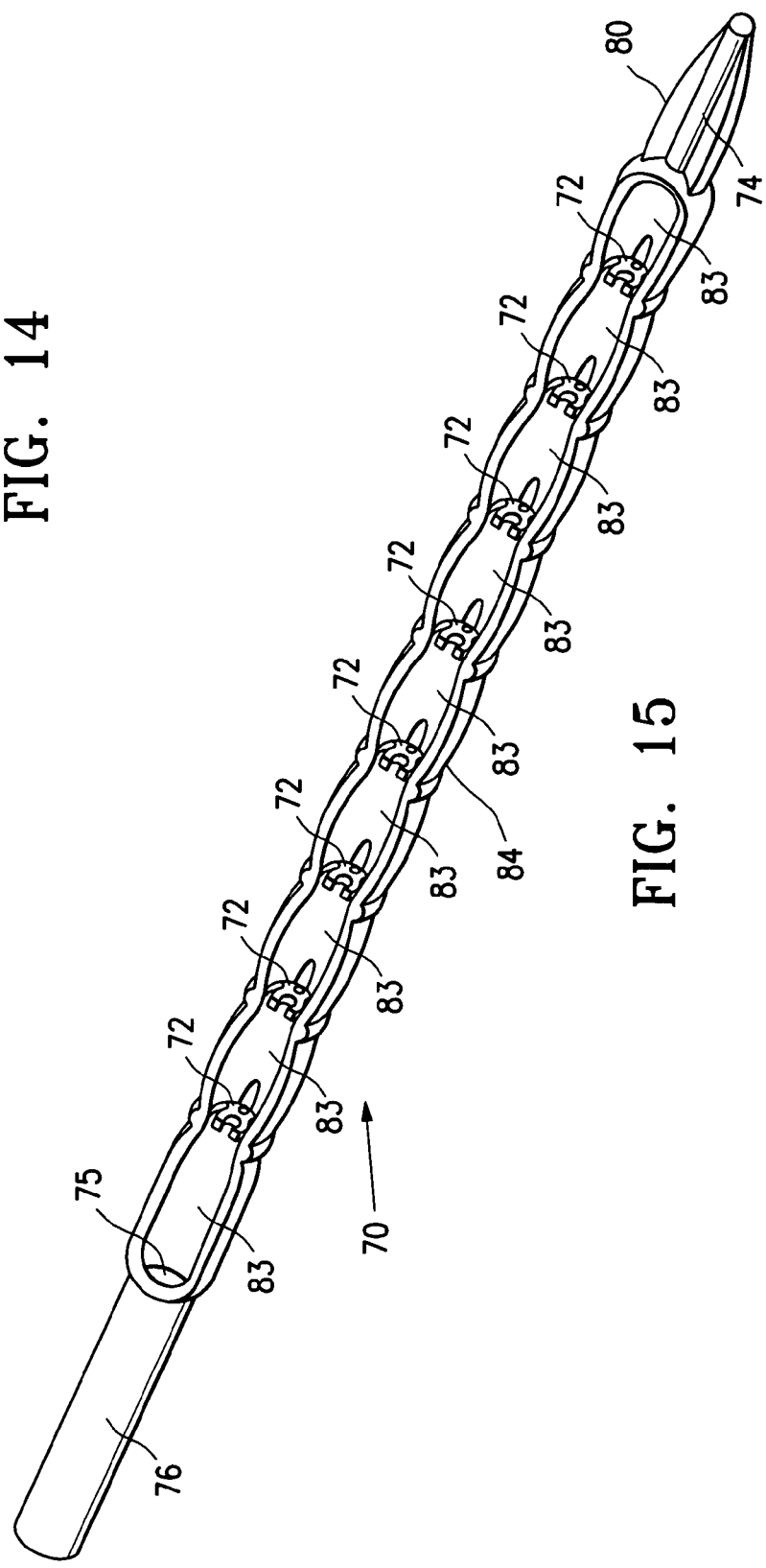
FIG. 14
FIG. 15

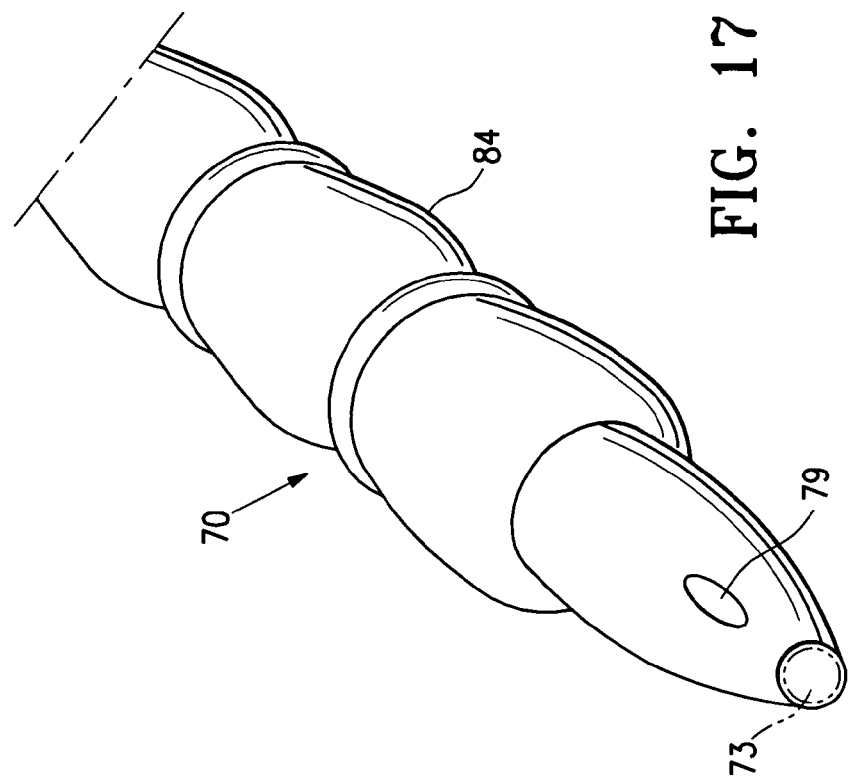
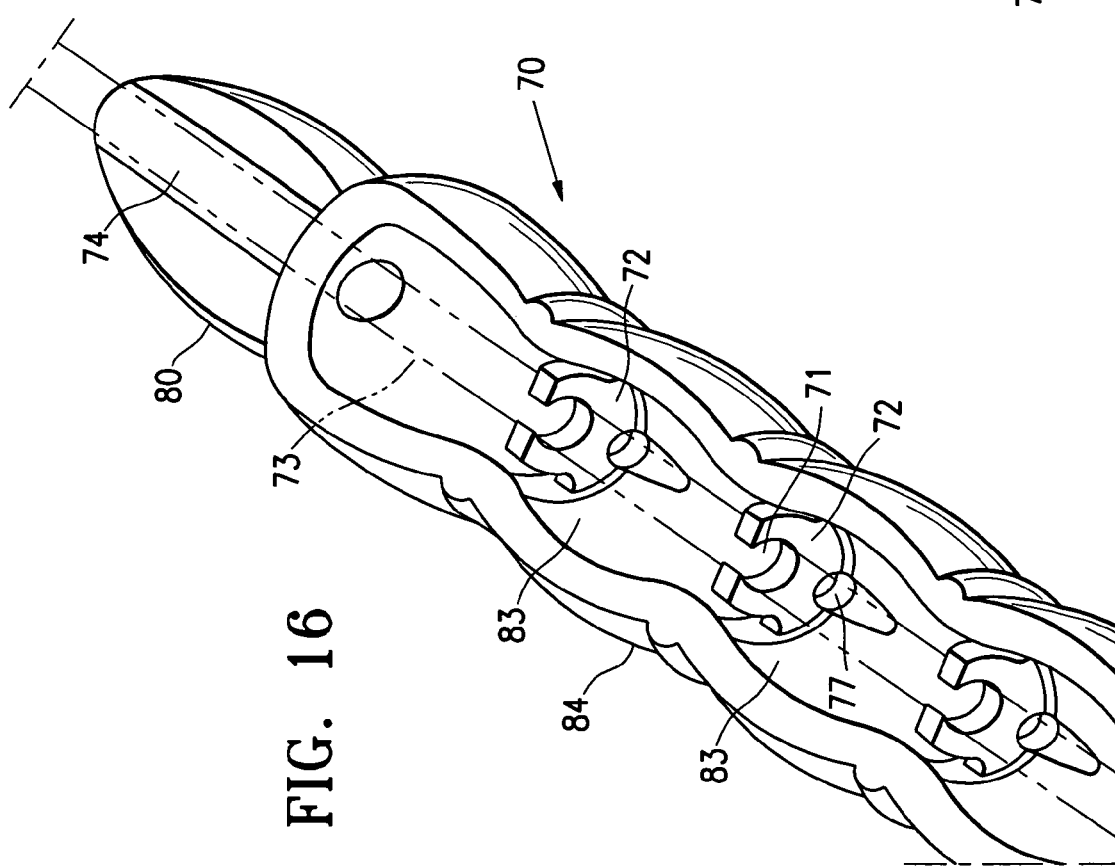
FIG. 16
FIG. 17

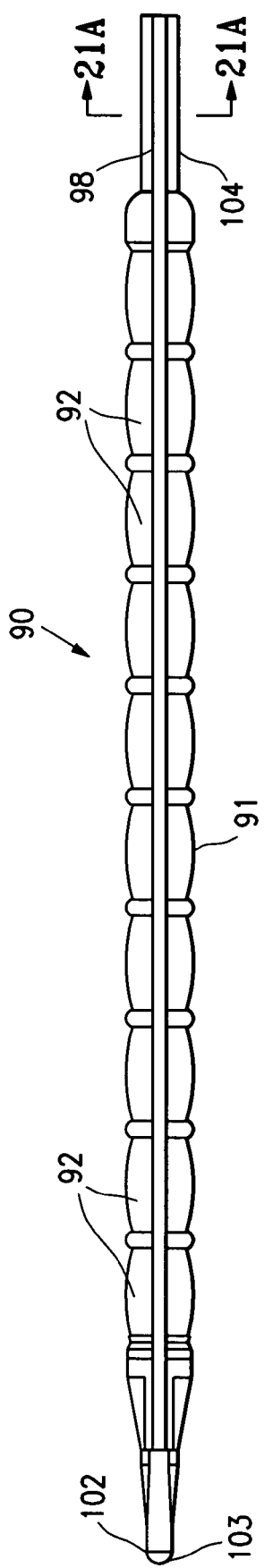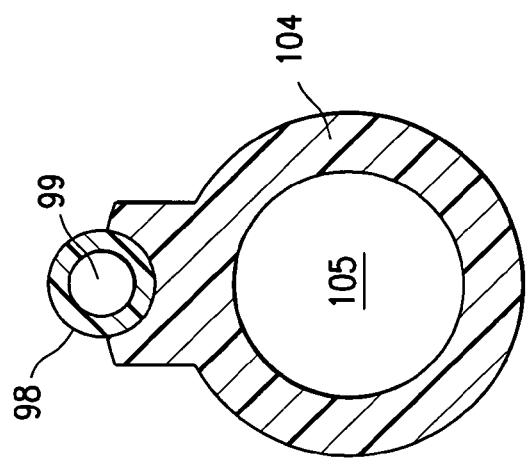
FIG. 21
FIG. 21A

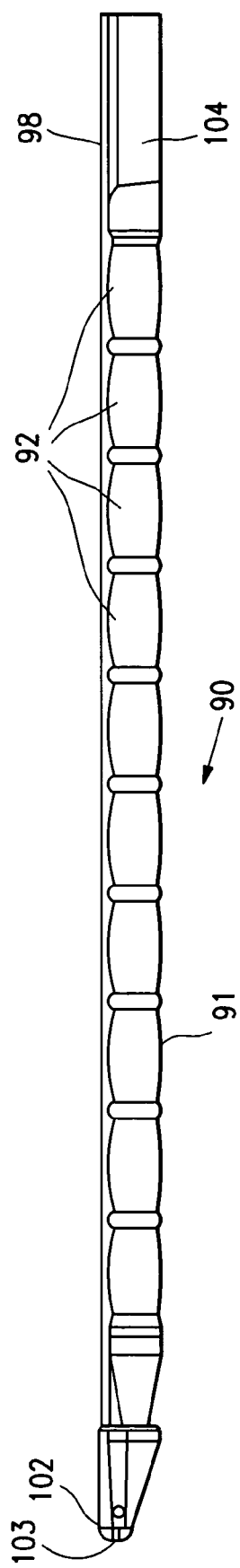
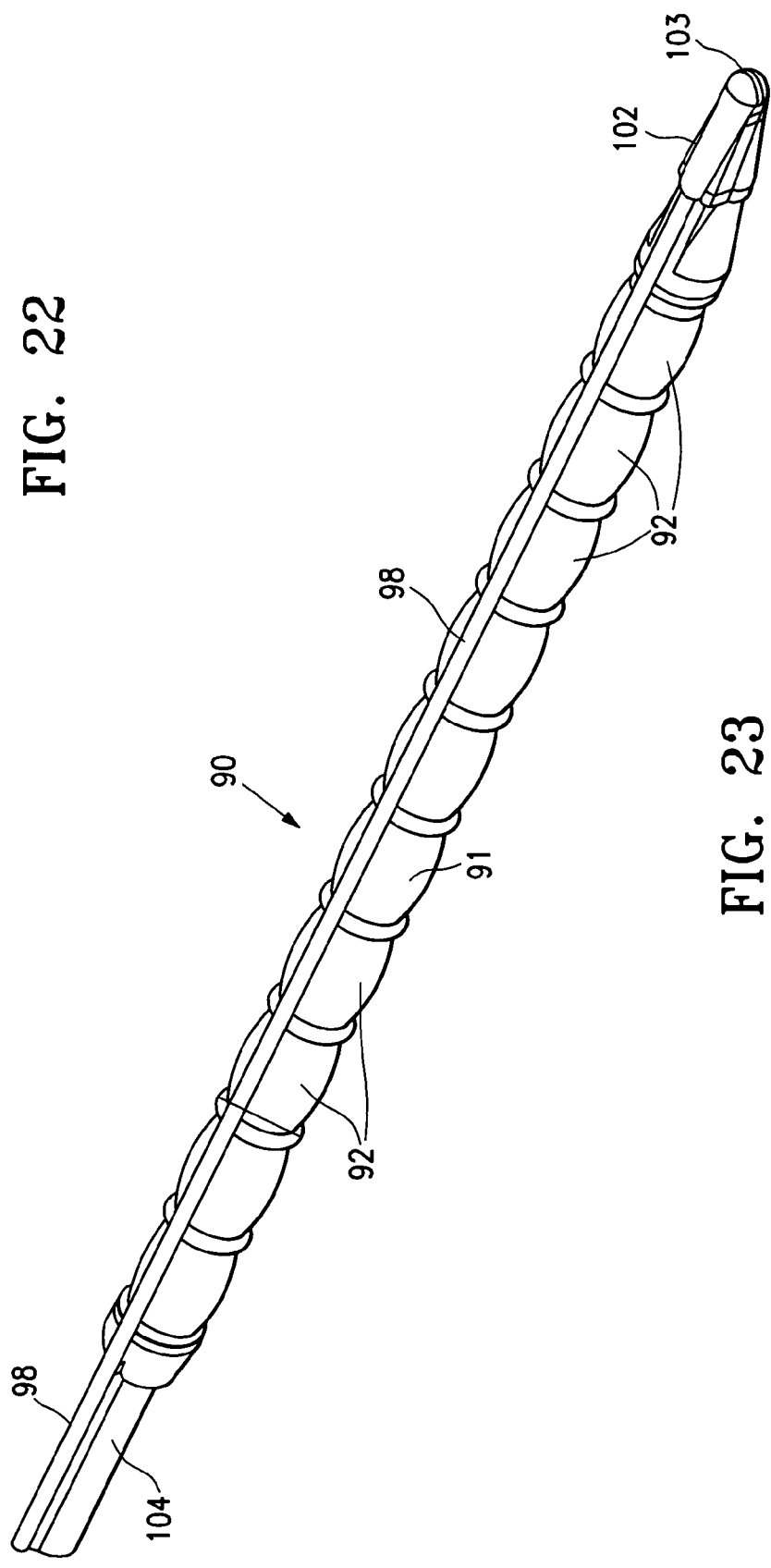
FIG. 22
FIG. 23

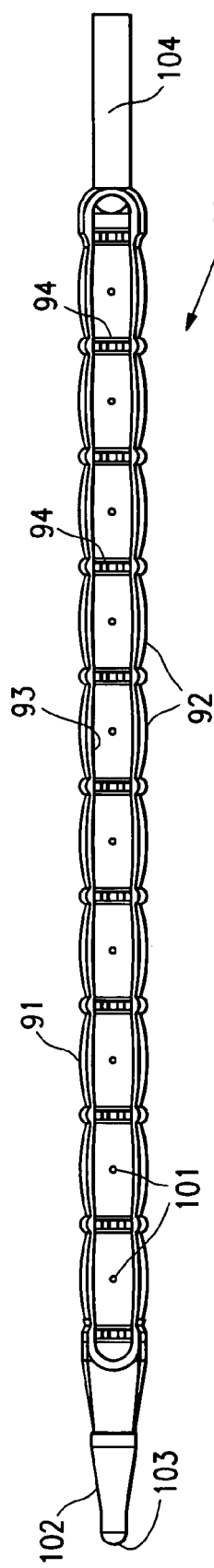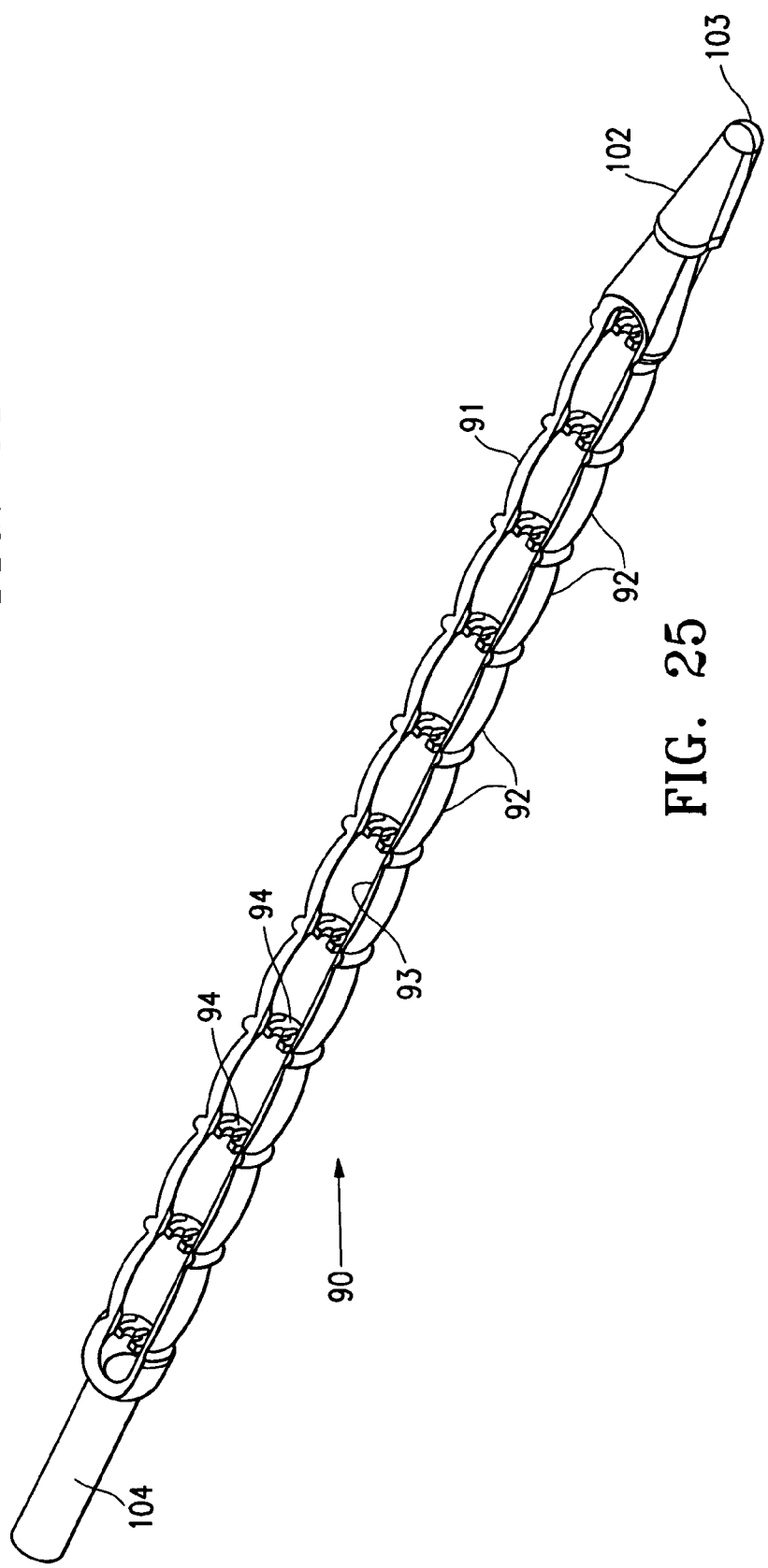
FIG. 24
FIG. 25

ABLATION PROBE WITH STABILIZING MEMBER

RELATED APPLICATIONS

This application is based on Provisional Application Ser. No. 60/571,081, filed on May 14, 2004, Provisional Application Ser. No. 60/602,415, filed on Aug. 18, 2004, and Provisional Application Ser. No. 60/614,703, filed on Sep. 30, 2004. These applications are relied upon for priority and are incorporated herein in their entireties by reference.

BACKGROUND OF THE INVENTION

This invention generally relates to surgical ablation probes and the use of such probes in the treatment of cardiac arrhythmia and particularly atrial fibrillation and atrial flutter.

Atrial fibrillation is the disorganized depolarization of a patient's atrium with little or no effective atrial contraction. Prior methods for treating a patient's arrhythmia include the use of anti-arrhythmic drugs such as sodium and calcium channel blockers or drugs which reduce the Beta-adrenergic activity. Other methods include surgically sectioning the origin of the signals causing the arrhythmia or the conducting pathway for such signals. However, the surgical technique is quite traumatic and is not suitable for a large number of patients. A more frequently used technique to terminate the arrhythmia involves ablating the heart tissue which causes the arrhythmia by a laser beam or high frequency electrical energy such as RF or microwave energy, to a desired arrhythmogenic site or pathway on the patient's endocardium. In the latter method, intravascular electrophysiological (EP) devices can be used to form lesions within a patient's atrial chamber to provide results similar to the surgical segregation techniques in terminating atrial fibrillation, but with significantly reduced trauma.

Typically, the ablation device is advanced within a patient's vasculature and into a heart chamber, and a lesion is formed on the endocardium when RF electrical energy is emitted from electrodes on the device. Typically, RF ablation techniques produce lesions of a small area, so that several lesions are typically formed to completely ablate an area. While these procedures of forming lesions from inside the heart chamber have met with some degree of success, there remains a need for suitable devices for forming such lesions in the patient's heart wall from the exterior thereof, particularly during a minimally invasive procedure while the heart is beating.

SUMMARY OF THE INVENTION

This invention is directed to a surgical ablation probe assembly for forming lesions at an intracorporeal location such as a surface of a patient's heart wall, and is particularly useful in forming linear and curvilinear lesions in a patient's heart wall to treat atrial arrhythmia. The method and device are particularly suitable for treating a beating heart.

An ablation probe assembly embodying features of the invention generally comprises an elongated ablation member with at least one ablation electrode on a distal shaft section thereof and a stabilizing member secured to the shaft distal section of the ablation member to secure the distal shaft section of the ablation member onto an intracorporeal site such as a surface of a patient's heart.

The stabilizing member generally has a proximal section and a distal section. The distal section has an inner chamber configured to receive the distal shaft section of the ablation member and a vacuum lumen leading to and in fluid communication with the inner chamber. A fluid delivery lumen may be provided that is in fluid communication with the inner chamber to provide fluid to the chamber. The distal section of the stabilizing member preferably has a stylet or obturator to stiffen the distal section and facilitate advancement of the assembly to the desired intracorporeal site. The stylet or obturator may be slidably disposed within the fluid delivery lumen or it may be provided with a separate lumen. The stylet or obturator is usually removed prior to final placement of the assembly at the intracorporeal site.

The elongated ablation member has an elongated shaft with a proximal shaft section, a distal shaft section and at least one ablation electrode, and preferably a plurality of ablation electrodes, on the distal shaft section which are configured to form a linear or curvilinear ablation pattern or lesion in a patient's heart wall. The distal shaft section of the ablation member may have at least about 4 and up to about 32 or more ablation electrodes, usually has about 6 to about 24 ablation electrodes. The distal shaft section of the ablation member is preferably shapeable or deflectable to facilitate advancing the device to the desired intracorporeal location and also shaping the distal section for forming lesions of desired shape. A suitable elongated ablation member for the probe assembly is the REVELATION® T-Flex device sold by the present assignee Cardima, Inc.

The stabilizing member is provided on at least a portion of the distal shaft section of the ablation member and is configured to be secured, preferably releasably secured to the distal shaft section. Upon the application of a vacuum to the interior of the stabilizing member, the reduced pressure holds the stabilizer to the patient's heart wall to ensure that at least one electrode of the ablation member engages the surface of the patient's heart when electrical power is directed to the ablation electrode. In one embodiment the distal shaft section has a plurality of electrodes to form a linear or curvilinear lesion or lesions in the wall of the patient's heart. The electrode size and spacing is preferably selected to provide a continuous lesion as described in U.S. Pat. No. 6,814,732, Patent Publication 2005/0015084 and Patent Publication 2002/0165532, all of which are assigned to the present assignee.

The stabilizing member has a surface configured to engage the patient's heart wall while pressing at least one ablation electrode against the exterior of the patient's heart wall to ensure electrical conducting engagement with the heart wall tissue when high frequency energy is applied to the one or more electrodes. Preferably, the stabilizing member has a vacuum lumen extending along at least a substantial length thereof and has at least one vacuum port which is in fluid communication with the vacuum lumen extending therein. Application of a vacuum within the interior of the stabilizer can aspirate fluid within or adjacent to the stabilizer and can also aid in securing the ablation probe against the patient's heart wall.

The stabilizing member preferably has a separate inner lumen extending along a substantial length thereof that is configured to receive the stylet or stiffening member which facilitates holding the stabilizer in a delivery configuration. The delivery configuration may be straight or curved or both to facilitate advancing the ablation assembly to the desired intracorporeal location such as through the space between the epicardial and pericardial layers of a patient's heart. Once the ablation assembly is in position, the stylet or stiffening member may be removed and the distal tip controlling mechanism of the ablation member may be used to shape the distal tip of the ablation assembly into a desired configuration.

The fluid delivery lumen of the stabilizing member extends along a substantial length thereof for delivering flushing or cooling fluid to the inner chamber of the stabilizing member. A discharge vent or opening may be provided in one or more segments of the stabilizing member for discharging fluid from the lumen in a desired manner into the interior chamber of the stabilizing member.

In one embodiment, the shape or deflection of the distal shaft section of the ablation member is controllable by a member on the proximal end of the device to form the desired configuration within a patient's body. This allows the ablation member to form one or more effective lesions of various shapes which replicate the MAZE procedure.

The one or more electrodes on the distal shaft section of the ablation member can be used as ablation electrodes to form a lesion on an intracorporeal surface within a patient's body when electrical energy, and preferably high frequency energy such as RF energy, is emitted therefrom. The ablation electrode(s) on the distal shaft section may be a combination ablation and sensing electrode, which is capable of ablation of tissue and detection of electrical activity from the patient's body. In a presently preferred embodiment, the ablation electrode on the distal shaft section is a helical coil for improved device flexibility, although other electrode designs are suitable including cylindrical bands, arcuate bands, ribbons or the like. One or more temperature sensors, such as a thermocouple, may be provided on the ablation member and are preferably disposed between ablation or sensing electrodes as described in U.S. Pat. No. 5,863,291 and U.S. Pat. No. 6,302,880 and application Ser. No. 09/847,181, filed May 1, 2001 (Pub. No. 2002/0165532). In one embodiment, the ablation member may include one or more electrodes for mapping and/or pacing on the shaft proximal and/or distal to the ablation electrodes. Preferably, the electrodes on the distal shaft section are configured for mono-polar use during ablation, and bipolar use during sensing, by use of a multiplexing switchbox. In the mono-polar sensing/pacing mode, a separate, return electrode which is not on the ablation member but which is in contact with the exterior surface of the patient's body is used.

In one embodiment, the stabilizer member is secured to the distal end of the ablation member and the assembly thus formed is introduced into the patient's thoracic cavity through an opening in the patient's chest wall, preferably through a trocar disposed in an intercostal space between the patient's ribs, preferably on the left side of the patient. The assembly is advanced within the patient's thoracic cavity and deployed so that the stabilizing member engages the exterior surface of the patient's heart. The epicardial space is usually small enough to hold the distal portion of the ablation assembly at the desired location. However, the application of a vacuum to the interior chamber(s) of the stabilizing member can facilitate holding the stabilizer and the exposed electrodes of the ablation device against a surface of heart wall, even when the heart is beating. The distal shaft section of the ablation member is preferably deflectable to facilitate shaping the distal portion of the assembly to form a lesion of a desired shape and location. Additionally, the distal end of the stabilizer member preferably has a light emitting element, such as a light emitting diode (LED) which allows the physician or other operating room personnel to locate the distal end of the stabilizer, ever when the distal tip of the stabilizer is disposed between the pericardial and epicardial layers of the patient's heart. If the distal end of the assembly emitting the light is not directly accessible, such as when disposed between the pericardial and epicardial layers, the physician can readily lance the pericardium, insert forceps and pull the distal end of the assembly to a desired region of the patient's heart. With the distal shaft section of the ablation member in a desired configuration, the electrodes are activated with electrical energy (RF) to form a linear or curvilinear lesion within the wall of the patient's heart. The ablation electrodes or separate sensing electrodes may be used to detect electrical activity from within the heart wall in order to determine the effectiveness of the lesion formation in treating the atrial fibrillation or flutter Accessing the heart in this manner allows the assembly to be advanced around the posterior side of the patient's heart and be guided around the right side of the heart to an anterior location. The physician may then grasp the distal end of the assembly and place the distal shaft section at a desired location. For example, the distal shaft section of the ablation member and stabilizing member secured thereto can be looped around the pulmonary vein and secured thereto. When RF energy is directed to the electrodes a lesion is formed around the vein.

These and other advantages of the invention will become more apparent from the following detailed description and the accompanying exemplary drawings.

BRIEF DESCRIPTION OF THE DRAWINGS

FIG. 11 is a top view of an alternative embodiment of a stabilizing member embodying features of the invention.

FIG. 12 is a side elevational view of the stabilizing member shown in FIG. 11.

FIG. 14 is a bottom view of the stabilizing member shown in FIG. 11.

FIG. 15 is an isometric view of the bottom of the stabilizing member shown in FIG. 11.

FIG. 16 is an enlarged isometric view of the distal portion of the bottom of the stabilizing member shown in FIG. 15.

FIG. 17 is an enlarged isometric front view of the stabilizing member shown in FIG. 11.

FIG. 21 is a top view of an alternative embodiment of a stabilizing member embodying features of the invention.

FIG. 21A is a transverse cross-section taken along the lines shown 21A-21A shown in FIG. 21.

FIG. 22 is a side elevational view of the stabilizing member shown in FIG. 11.

FIG. 23 is an isometric view of the stabilizing member shown in FIG. 21.

FIG. 24 is a bottom view of the stabilizing member shown in FIG. 21.

FIG. 25 is an isometric view of the bottom of the stabilizing member shown in FIG. 21.

DETAILED DESCRIPTION OF THE INVENTION

FIGS. 1-8 illustrate a surgical ablation probe assembly 10, embodying features of the invention, which generally comprises an ablation member 11 and a stabilizing member 12.

Figure 9:
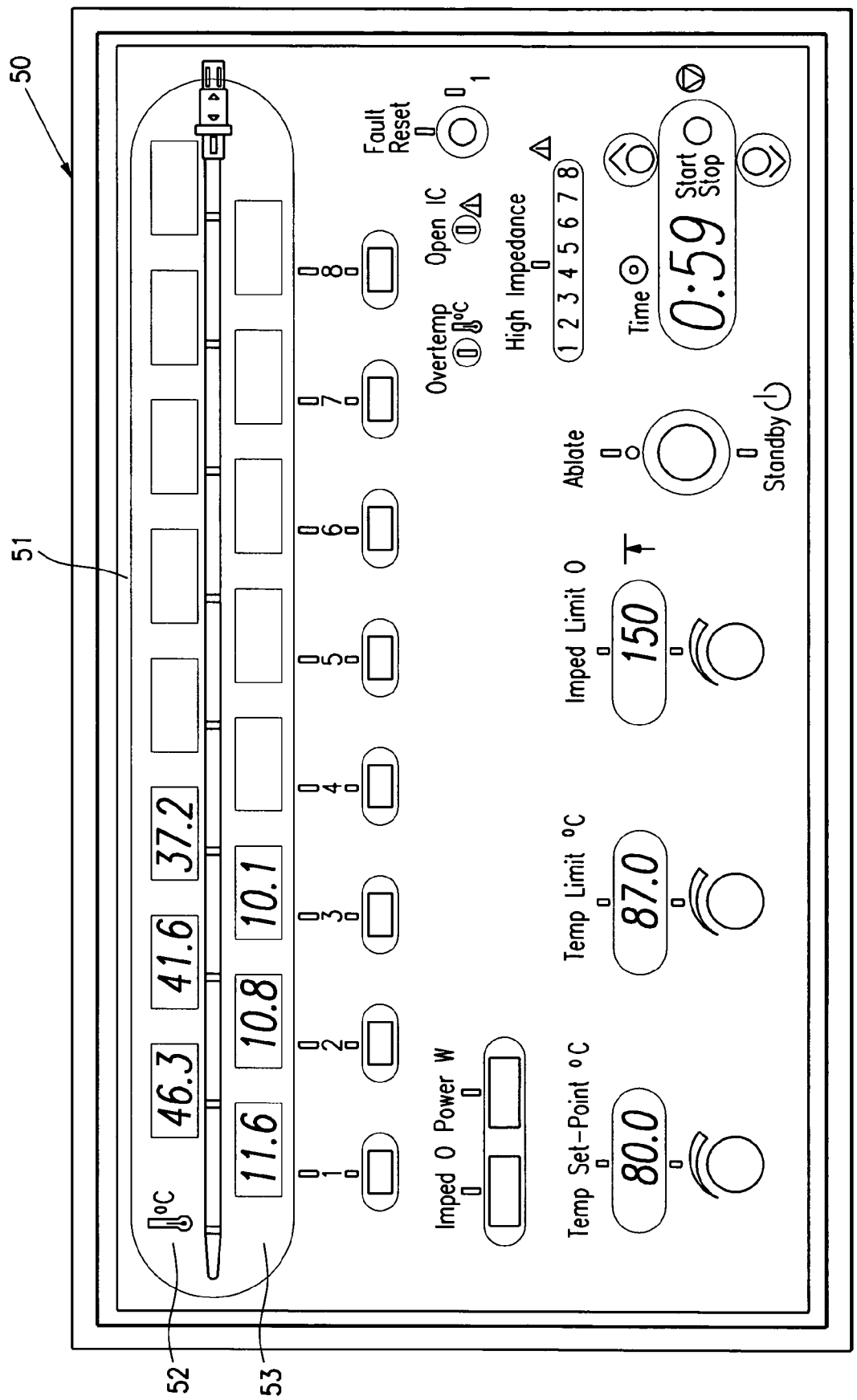
FIG. 9 is a front view of an energy source for the ablation member shown in FIG. 1.

The ablation member 11 has an elongated shaft 13 with a proximal shaft section 14, a distal shaft section 15, and a plurality of ablation electrodes 16 on the distal shaft section 15. A handle 17 is secured to the end of the proximal shaft section 14 which has an electrical connector 18 adapted to be secured to an RF energy source (such as shown in FIG. 9). The handle 17 has a finger operated ring 20 for adjusting the shape of the distal shaft section such as the curved structure shown as 15A. The distal shaft section 15 has a flexible distal tip 21 distal to the electrodes which is adapted to guide the distal end of the ablation member into the guideway of the stabilizing member 12. Suitable commercial products for the ablation member include the REVELATION® T-Flex, a deflectable micro catheter with eight electrodes and 2-2-2 mm electrode spacing which is available from the assignee Cardima, Inc. Further details of the ablation member may be found at http://www.cardima.com.

The stabilizing member 12 has an elongated shaft 22 with a proximal shaft section 23, a distal shaft section 24 and a distal tip 25 configured to facilitate advancing the stabilizing member about the desired intracorporeal locations. The distal shaft section has a plurality of securing pods 26 which have concave, tissue engaging surfaces 27 provided with vacuum ports 28. A vacuum lumen 30 (Shown in FIG. 6) extends through the proximal shaft section 23 and distal shaft section 24 configured to transfer a vacuum to the distal shaft section 24. Tubules 31 are provided to transfer the vacuum within vacuum lumen 30 to the vacuum ports 28.

The concave, tissue engaging surfaces 27 of securing pods 26 are configured to engage the tissue of the patient's heart, e.g. epicardial tissue, so that the vacuum acting through the vacuum port holds the pod and engaged tissue in a stabilized relationship even though the heart may be beating. The transverse dimensions of the fluid connection between the vacuum lumen 30 and the tubules 31 and the transverse dimensions of the tubules themselves may be adjusted so that if the vacuum is broken at one or more of the vacuum ports, all vacuum (and as a result stabilization) is not lost.

Figure 7:
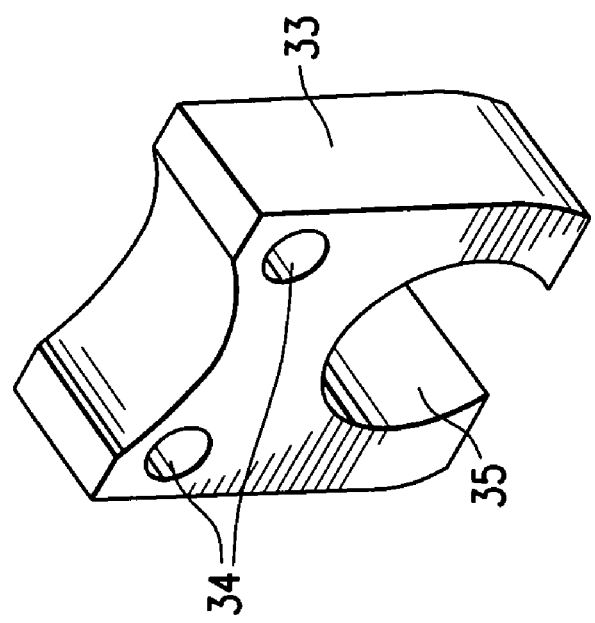
FIG. 7 is a perspective view of a C-clamp prior to molding into the stabilizing member.

The securing pods 26 are provided with a recess 32 configured to securely receive the distal shaft section 15 of the ablation member 11. As shown more clearly in FIGS. 4 and 5 clips 33 are provided between at least some adjacent pods 26 to more securely hold together the distal shaft section of the ablation member and the stabilizing member. Clips 33 are preferably preformed of tough, high strength polymeric material (e.g. Nylon), such as shown in FIG. 7, and molded in place with the much softer polymeric material of the distal shaft section 24 of the stabilizing member 12. Passageways 34 are provided in the base of the clip 33 to ensure a sound mechanical connection between the harder clip and the distal shaft section 24 of the stabilizing member 12. The clips 33 have recesses 35 which are preferably aligned with the recesses 32 in the pods 26 and configured to receive the distal shaft section 15 of the ablation member 11. The recesses 35 in the clips 33 more firmly grip the distal shaft section 15 than the recesses 32 in the pods 26 due to the increased stiffness of the material from which the clips 33 are made. The recesses 32 and 35 are configured to receive the ablation member 11 but allow the ablation electrodes 16 to extend out of these recesses to more readily contact tissue when a vacuum is pulled in the vacuum lumen. The cylindrical outline 36 of an ablation electrode 16 is shown in phantom in FIG. 6. The recesses 32 and 35 are configured to enable the stabilizing member 12 to slide over the ablation member 11, yet grip the ablation member with enough frictional force to hold the ablation member. The openings 37 between the vacuum lumen 30 and the vacuum tubules 31 are preferably flow restrictive openings such as slits to help maintain a vacuum within lumen 30 when the vacuum is broken at one of the vacuum ports 28. The upper surfaces of recesses 32 are provided with a groove 38 for venting gases which may be generated during the lesion formation.

The securing pods 26 are longitudinally spaced from each other and provided with rounded ends to ensure the desired motion (e.g. deflection) of the distal shaft section 24 of the stabilizing member 12. Preferably, the distal shaft section 24 of the stabilizing member 12 is sufficiently flexible to follow or conform to the shape of the distal shaft section 15 of the ablation member 11 as its shape is adjusted to provide the desired lesion shape. Suitable polymeric materials for the stabilizing member 12 include a low durometer (30-60) silicone or polyurethane. The polymeric material is preferably biocompatible and sterilizable.

Figure 4:
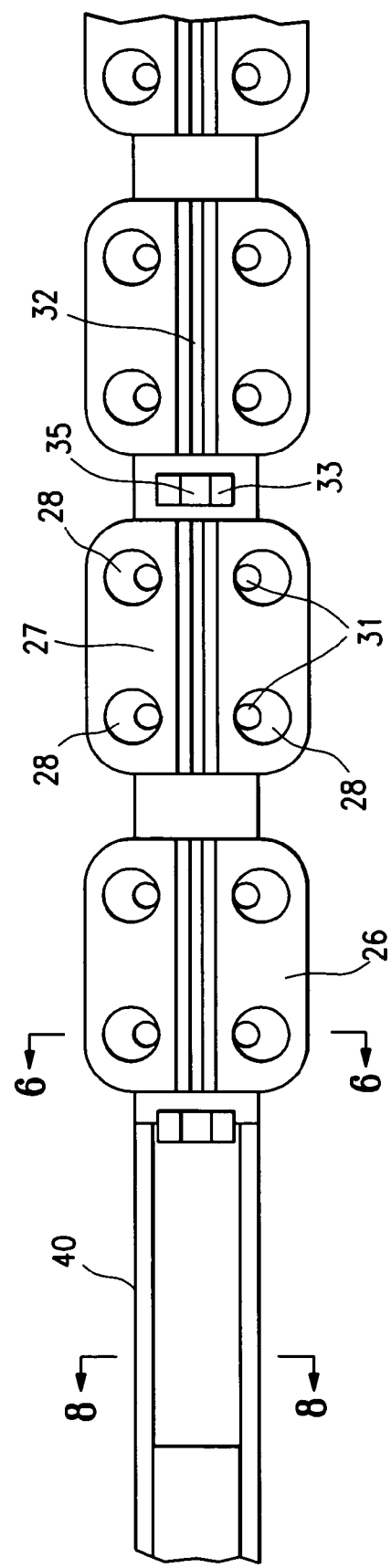
FIG. 4 is an enlarged view of the stabilizing member shown in FIG. 3 within the circle 4-4.
Figure 5:
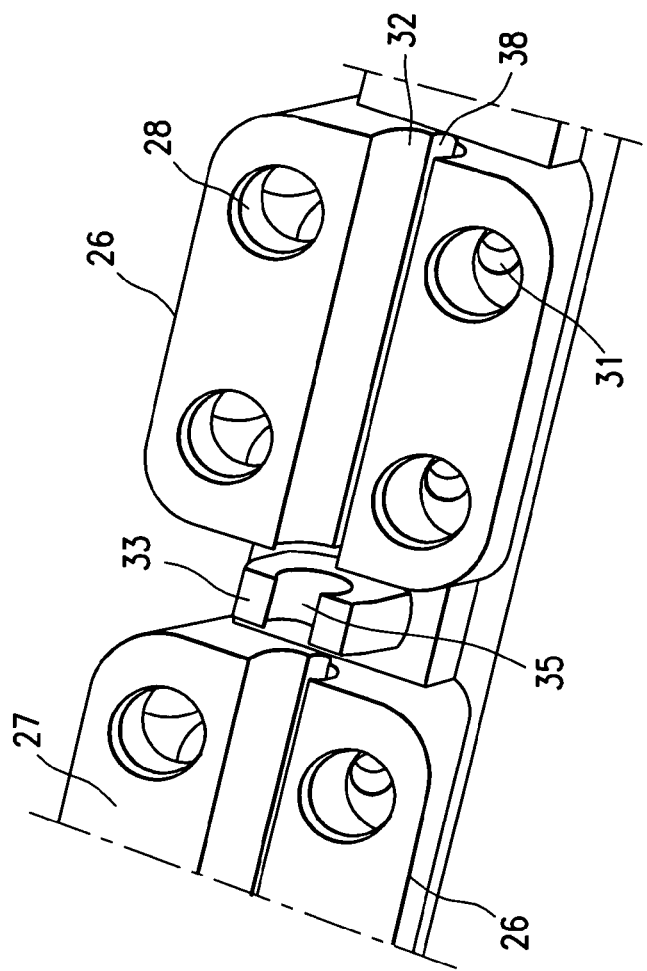
FIG. 5 is an enlarged, partial perspective view of the stabilizing member shown in FIG. 3.
Figure 6:
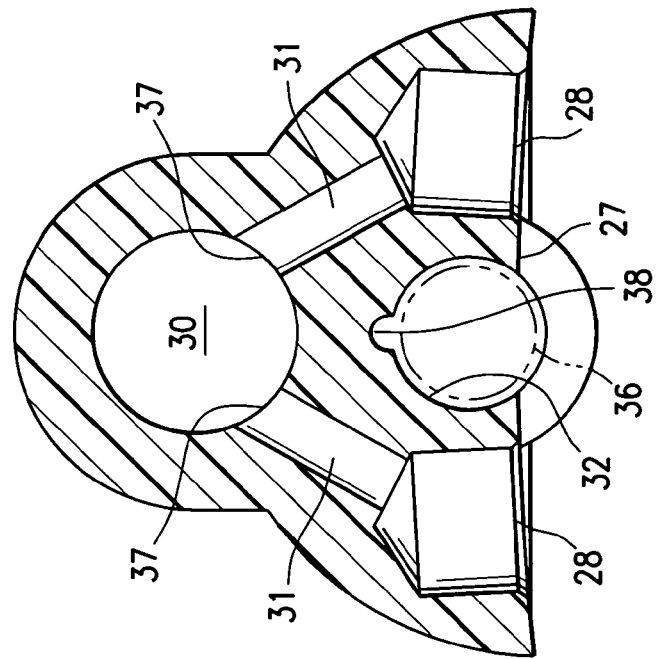
FIG. 6 is a transverse cross-sectional view of the stabilizing member shown in FIG. 1 taken along the lines 6-6.
Figure 8:
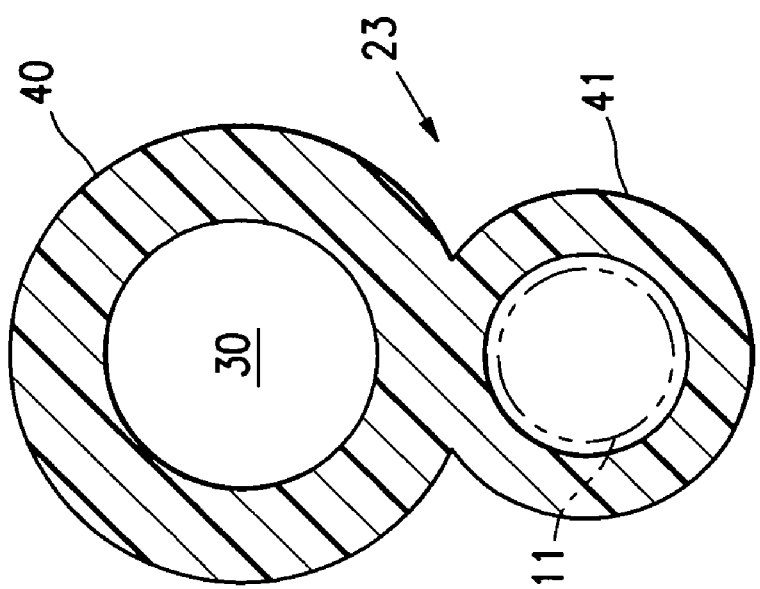
FIG. 8 is a transverse cross-section taken along the lines 8-8 in FIG. 4.

FIG. 8 illustrates the cross-section of the proximal shaft section 23 of the stabilizing member 12 taken along the lines 8-8 shown in FIG. 4. The proximal shaft section 23 has an upper cylindrical portion 40 which defines in part the vacuum lumen 30 and which continues along the length of the stabilizing member 12 to the most distal securing pod 26. The proximal shaft section 23 also has a smaller cylindrical portion 41 which slidably receives the ablation member 11 shown in phantom and guides the ablation member to the recess 32 in the securing pods 26.

The electrical connector 18 is preferably a multi-pin connector and is configured to be electrically connected with a multi-channel energy management device 50 such as shown in FIG. 9. The RF energy controller 50 shown in FIG. 9 is the INTELLITEMP® RF Energy Controller available from the present assignee, Cardima, Inc. The display panel 51 of the energy controller 50 illustrates the tissue temperature (top portion 52 of panel) and the energy (bottom portion 53 of panel) for the electrodes which are receiving RF energy. Further details of the energy controller can be found at http://www.cardima.com.

Figure 10:
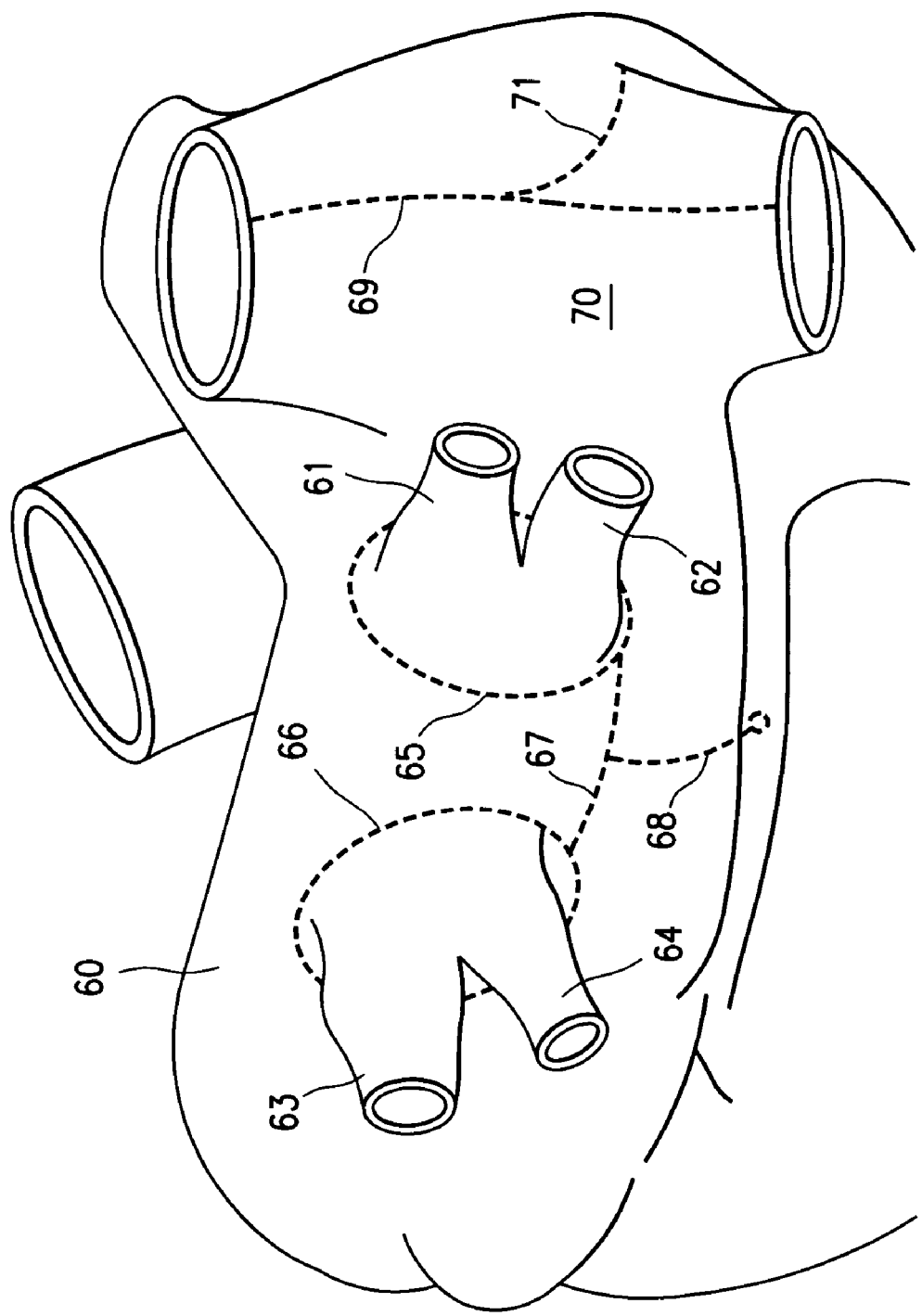
FIG. 10 is a schematic representation of a top posterior portion of a patient's heart illustrating the linear and curvilinear lesions formed for the MAZE procedure.
Figure 13:
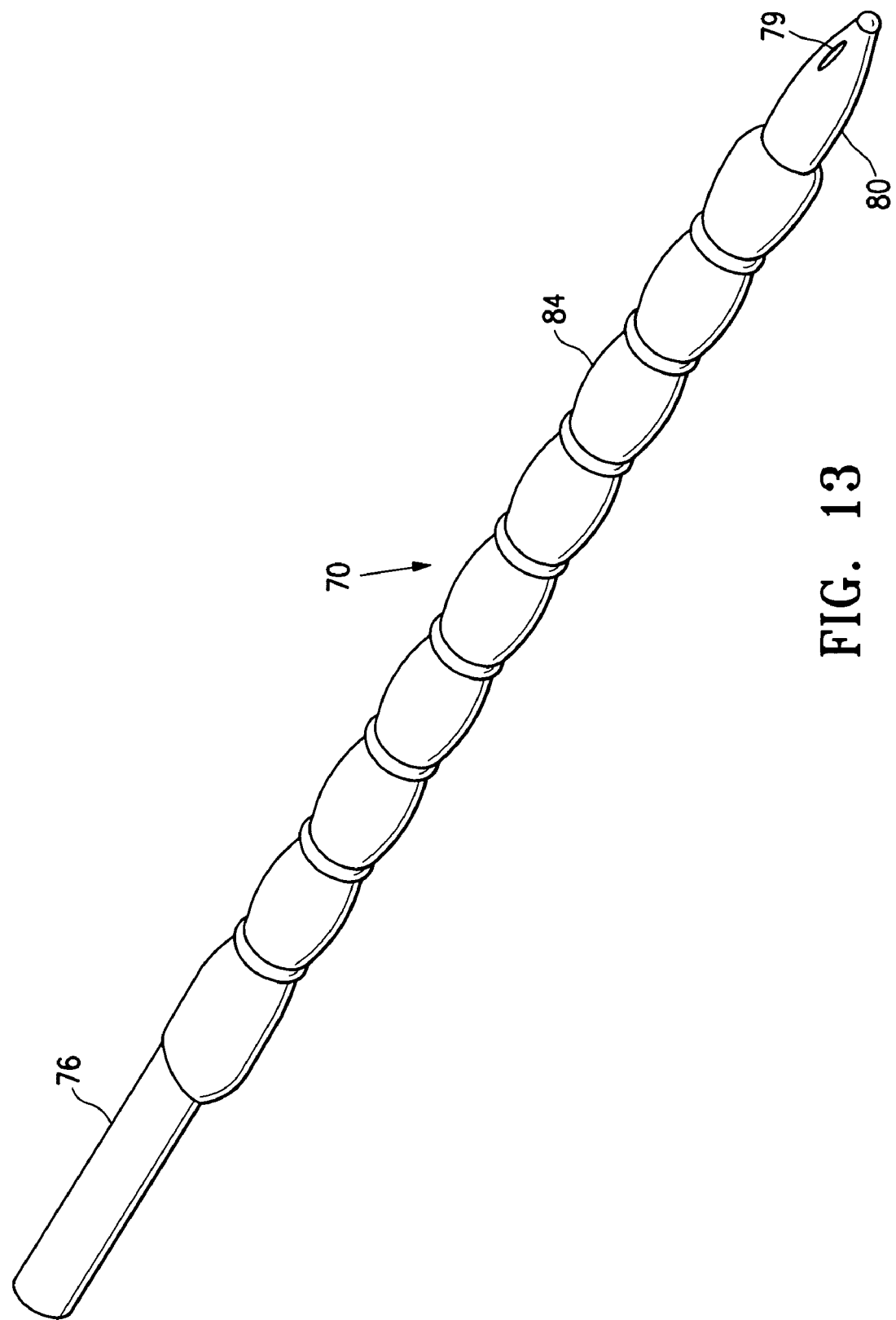
FIG. 13 is an isometric view of the stabilizing member shown in FIG. 11.

In a method of treating a patient for atrial fibrillation or flutter, the ablation probe embodying features of the invention may be used to form a linear or curvilinear lesion, particularly a continuous lesion, extending around an exterior surface of the patient's pulmonary vein. FIG. 10 schematically illustrates the upper posterior surface of a patient's heart 60 with the right pulmonary veins 61 and 62 and the left pulmonary veins 63 and 64. Dotted lines show the lesions required to replicate the surgical MAZE procedure. One lesion line 65 encircles the right pulmonary veins 61 and 62. Lesion line 66 encircles left pulmonary veins 63 and 64. Lesion line 67 extends between the right and left pulmonary veins and lesion line 68 extends downwardly from and perpendicular to lesion line 67. Longitudinally oriented lesion line 69 extends along the junction between the inferior and superior vena cava 70. Lesion line 71 extends at an angle from lesion line 69. The surgical ablation probe 10 embodying features of the invention can successfully form the lesions indicated above on a patient's heart 60. An ablation probe assembly embodying features of the invention may be utilized to form lesions at other locations and may be used to form lesions having different shapes.

The ablative MAZE procedures can be performed through a trocar disposed in an intercostals space on the left side of the patient. Other openings such as a mini-thoracotomy may be employed for introducing the assembly in a minimally invasive manner through the chest wall. Once introduced into the patient's chest wall through a trocar, the assembly may be manipulated to place the distal shaft sections of the ablation member and the stabilizing member in a desired location on the epicardial surface of the patient's heart. A vacuum is applied to the interior of the stabilizer to secure the ablation probe assembly to the beating heart wall. If needed, a long handled clamp such as a hemostat may be used to position the distal tip of the assembly in a desired location. Stabilization of the ablation member against the heart wall ensures good electrical contact for ablation and also effective temperature sensing of the heart tissue adjacent to the temperature sensor.

The ablation electrodes 16 on the distal shaft section 15 are powered with RF electrical current to form a lesion(s) extending at least in part along the lesion lines indicated above. The position of the lesion is preferably chosen to interrupt the conduction path to the atrium based upon the mapping of the atrial wall. Alternatively, the lesion may be located to ablate the actual focal origin in the pulmonary vein.

Typically, RF current is delivered to two to eight electrodes to perform a first ablation and then to adjacent electrodes, two to eight electrodes at a time, until a linear, curvilinear or circumferential lesion of desired length is obtained on the epicardial surface. The temperature sensors can be used to detect the temperature of the tissue of the heart wall between the adjacent electrodes, to control the high frequency energy. Additionally, feedback of the temperature data can be used to modulate the energy and prevent coagulum formation in some applications, and cooling fluid can also be used. After the ablation, the electrodes 16 can be employed to detect electrical activity to ensure that the ablation has been effective in terminating the fibrillation or flutter.

The ablation probe 10 can be used to form linear, curvilinear or circumferential lesions.

Each ablation electrode 16 is spaced apart from one or more adjacent electrode 16 on the distal shaft section 15. However, depending on the duration and energy level used during an ablation procedure, the lesion(s) formed by electrodes 16 can be discontinuous or alternatively, can be joined together and thus continuous.

The ablation member 11 of the ablation probe assembly 10 has a total length, excluding the handle 17, of about 70 cm to about 90 cm, and preferably between about 80 and 90 cm, e.g. about 86.5 cm. The length of the distal shaft section 15 having ablation electrodes depends upon the number of electrodes present but generally is about 1 cm to about 25 cm, and preferably about 4 to about 20 cm. The outer diameter of the distal shaft section 15 of the ablation member is typically about 1.0 mm (3.0 French) to about 2.0 mm (6.0 French), and preferably about 1.3 mm (4 French) to about 1.7 mm (5 French). The maximum outer dimensions of the electrodes are generally about 1.0 mm (3 Fr) to about 1.3 mm (4 French), and preferably about 1.22 mm (3.7 French). The electrode length is about 0.2 mm to about 10 mm, and preferably about 3 to about 8 mm, e.g. about 6 mm. The inter-electrode spacing is generally about 0.2 mm to about 4 mm, and preferably about 0.5 to about 3 mm. In a presently preferred embodiment, the inter-electrode spacing is uniform. However, the electrode spacing may alternatively be non-uniform. About 8 to 32 individual electrodes, preferably 16-24 electrodes, are provided on the shaft distal section, however, the device may have a greater or lesser number of electrodes. Further details of an electrodes suitable for devices embodying features of the invention may be found in U.S. Pat. No. 5,863,291 and U.S. Pat. No. 6,302,880 and application Ser. No. 09/847,181, filed May 1, 2001 (Pub. No. 20020165532), (all assigned to the present assignee).

Figure 19:
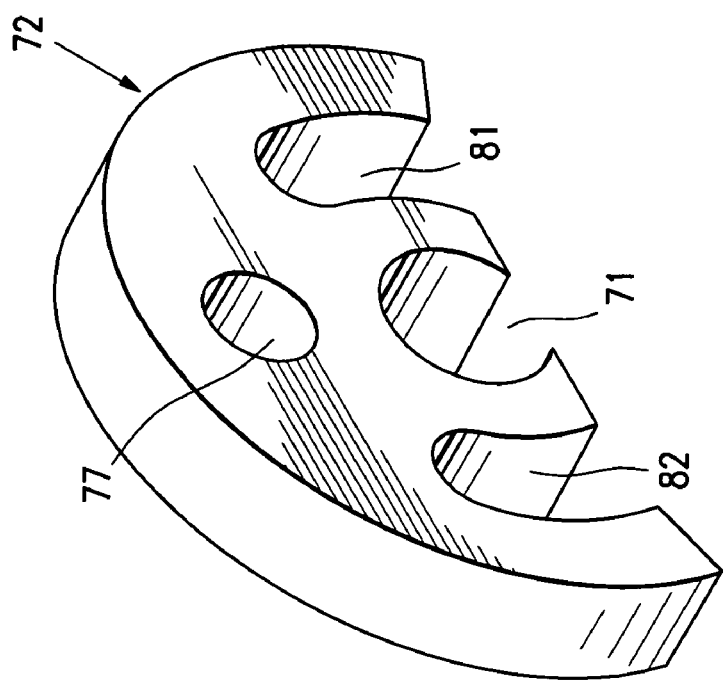
FIG. 19 is an isometric view of the clip used to segregate the interior of the stabilizer member into separate chambers.
Figure 18:
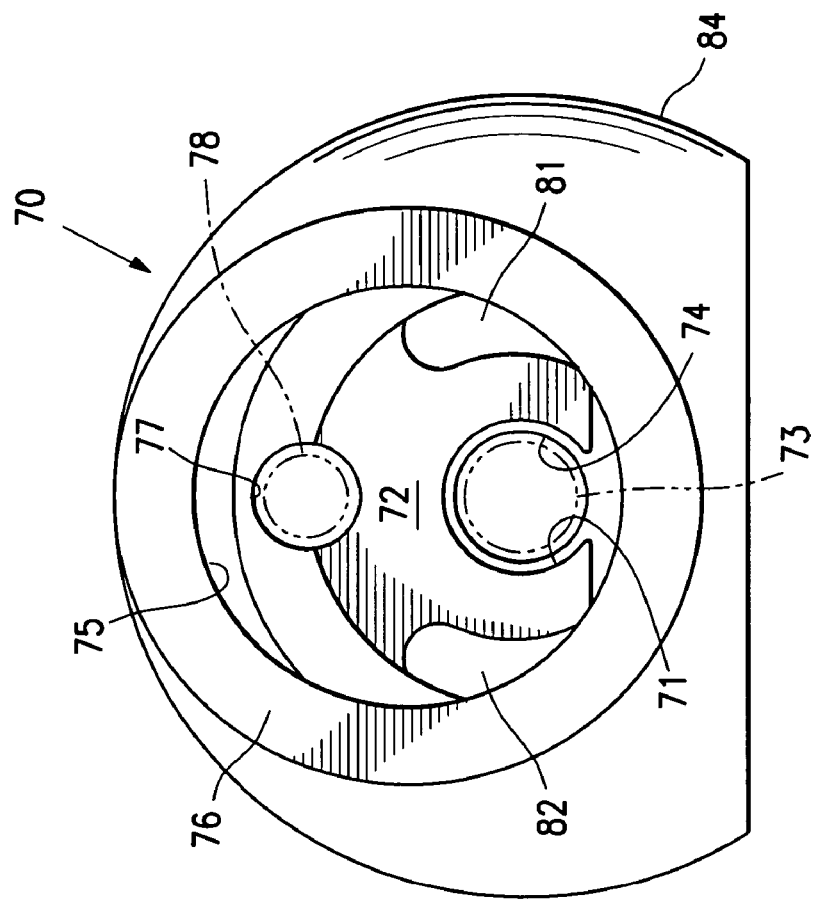
FIG. 18 is an enlarged back view of the stabilizing member shown in FIG. 11.

FIGS. 11-19 illustrate a stabilizing member 70 which is similar in function to the embodiment shown in FIGS. 1-10. In stabilizer member 70, recess 71 of clip 72 is configured to receive electrophysiology (EP) or ablation member 73 (shown in phantom in FIG. 16) in a snap fit. (Note that the clips 72 are only partially shown in FIG. 16) The clip 72 is best shown in FIG. 19. The distal end of the EP member 73 (the same as ablation member 11) fits into passageway 74, best shown in bottom view (FIG. 14). The EP member 73 is inserted into the stabilizing member 70 through the inner lumen 75 of the proximal shaft section 76. A fiber optic 77 extends in the stabilizing member 70 through the proximal shaft section 76 and is disposed in passageways 77 in the clips 72. The distal end of fiber optic 78 extends into the hole 79 provided in the tapered distal end 80 of the stabilizing member 70 to illuminate the intracorporeal tissue site or sites the system is advanced through or positioned within. The proximal end (not shown) of the fiber optic 78 is optically connected to a light source. The light source may emit coherent or incoherent light Alternatively, a light emitting diode or other light emitting member such as a suitable light bulb may be provided in the distal end with a suitable electrical conductor extending back to the proximal end of the device through passageways 77 of clips 72 where the conductor may be electrically connected to an electrical energy source. The light emitter in the distal end of the stabilizing member 70 may be provided with a light dispersing member (not shown) if a more dispersed light beam is desired.

A vacuum is applied to the interior of the stabilizing member 70 through passageway 75 in the proximal shaft section 76 or a separate lumen (not shown) and is maintained throughout the interior of the stabilizing member 70 through openings 81 and 82 of the clips 72 to maintain a vacuum in the chambers 83 defined in part by one or a pair of clips 72. The assembly of stabilizing member 70 and EP member 73 is operated in essentially the same manner as the embodiment shown in FIGS. 1-10.

The shell 84 of the stabilizer 70 has a segmented design with the segments having a bowed configuration which allows a suction seal to be maintained at different curves and narrow curve reaches of the EP member 73. The bowed segmented shell design accommodates the bending tensile and compressive stresses and avoids wrinkle or crease formation. The integrated clips 72 act as stiffening ribs at the ends of the segments and ensure adequate airflow through the sheath. The recess 71 securely holds the EP member 73 and allows enough surface area of the electrodes exposed so that electrical energy to tissue is not hindered.

The distal end of an ablation member (not shown but the same as or similar to ablation member 11) fits into passageway 105 which leads the ablation member to the recesses 95 of clips 94. The LED 103 is provided in the distal tip 102 of the stabilizing member 90 to illuminate an intracorporeal tissue site or sites the system is advanced through or positioned within. Conductors (not shown) may extend through the wall of the stabilizer 90 to direct electrical energy to the LED.

Figure 20:
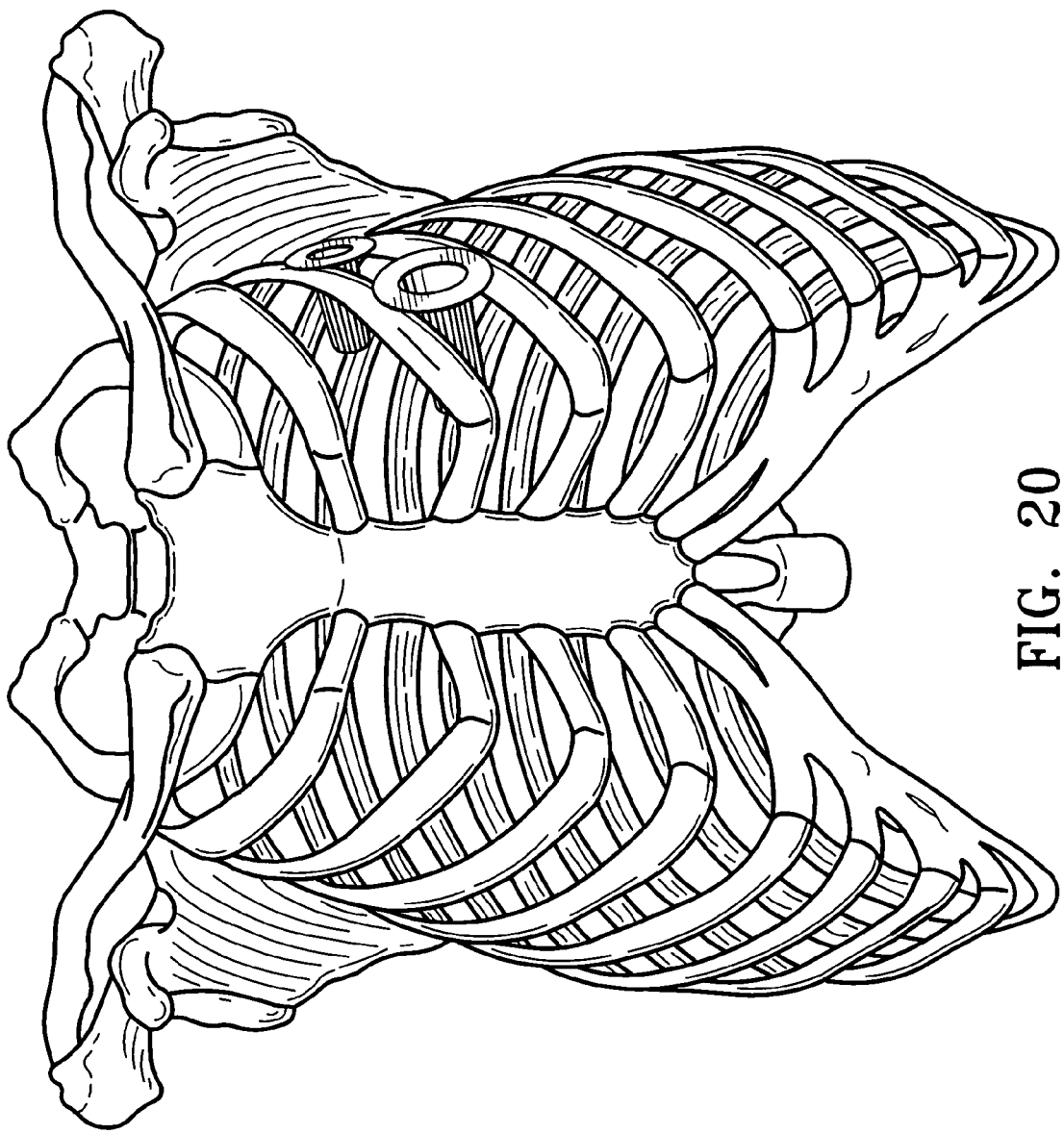
FIG. 20 is a front view of a rib cage with a trocar disposed within an intercostals space to facilitate introducing the ablation assembly into the patient's thoracic cavity.
Figures 26, 27:
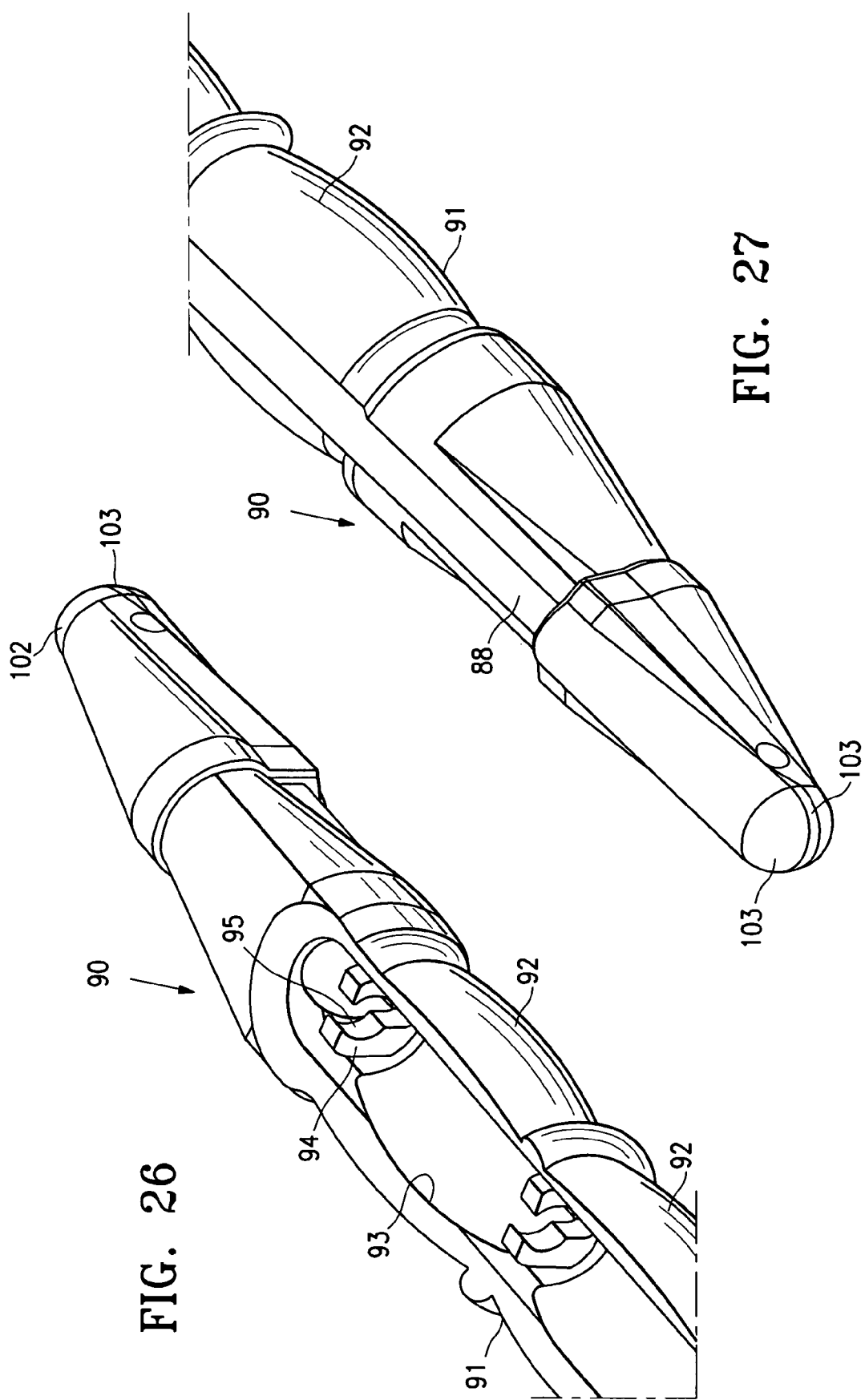
FIG. 26 is an enlarged isometric view of the distal portion of the bottom of the stabilizing member shown in FIG. 25.
FIG. 27 is an enlarged isometric front view of the stabilizing member shown in FIG. 21.
Figure 29:
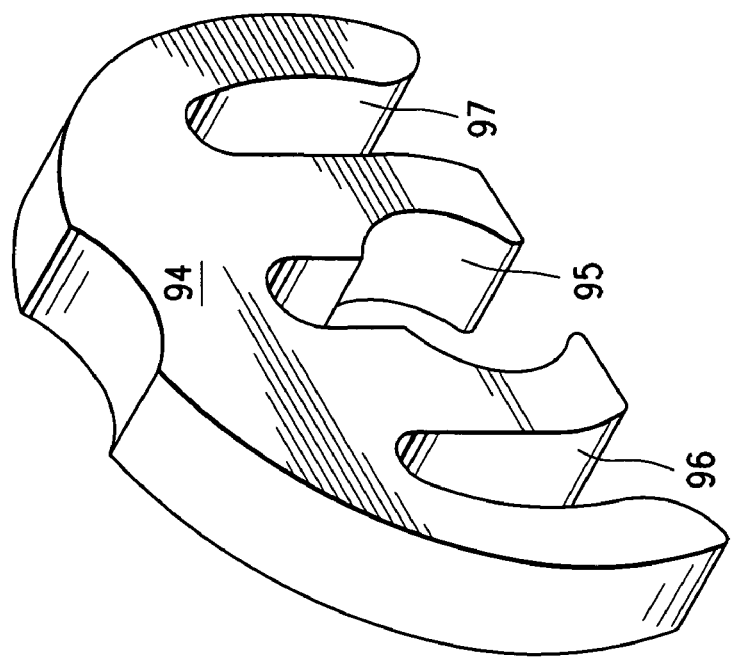
FIG. 29 is an isometric view of the support element used to support the ablation member within the interior of the stabilizer member.

This embodiment allows deployment and manipulation of the assembly from one side of the patient, preferably through a trocar such as schematically shown in FIG. 20. The assembly is advanced around the posterior side of the heart, preferably through a delivery sheath or cannula. The distal end of the delivery sheath is preferably disposed on the right side of the posterior portion of the heart. When the distal portion of the assembly is advanced around the anterior side of the patient's heart, the light on the distal end of the EP member is readily seen by the physician even when disposed between the epicardial and pericardial layers of the patient's heart. The physician may then grasp the distal end of the assembly and place the active portion thereof at the desired location, such as surrounding the patient's pulmonary vein where a continuous lesion is preferably formed to effectively treat atrial fibrillation or flutter.

Figure 1:
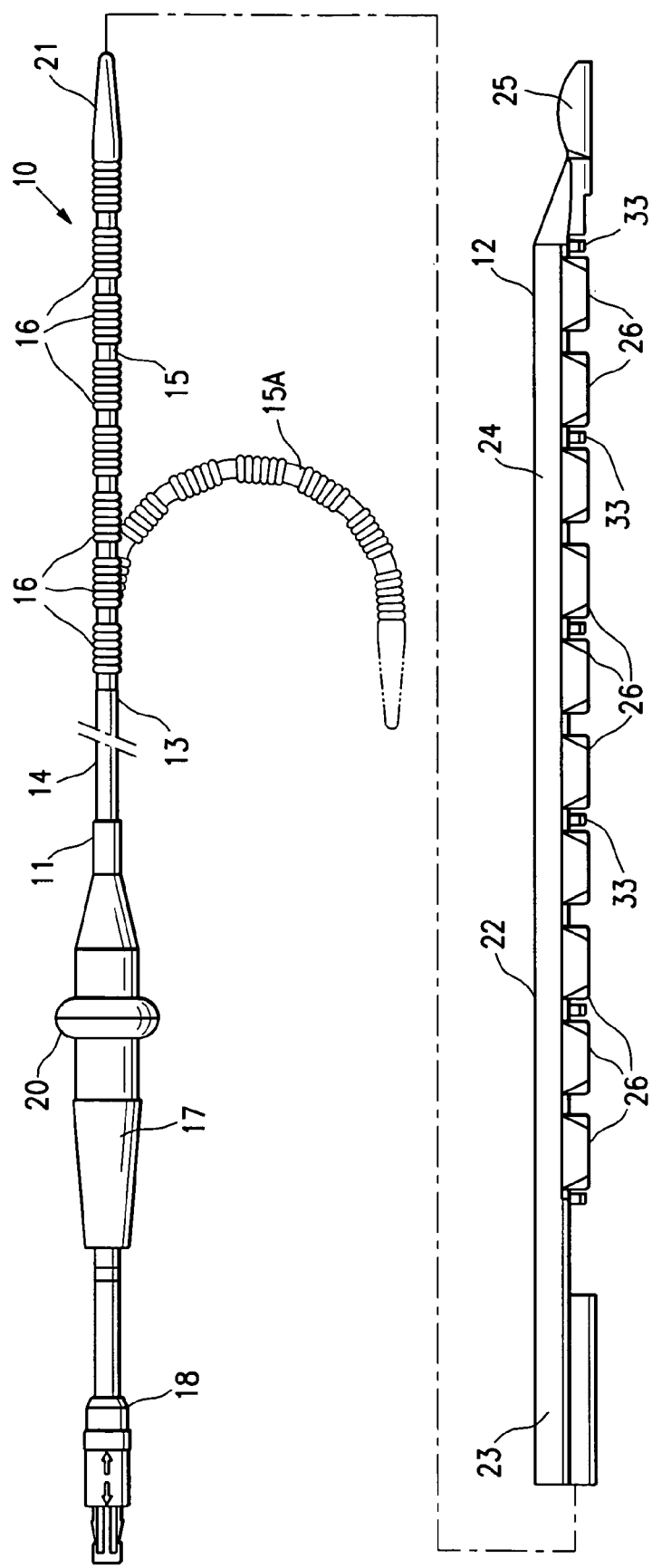
FIG. 1 is an elevational view of an ablation probe assembly embodying features of the invention with an ablation member and a stabilizing member of the assembly disassembled.
Figure 2:
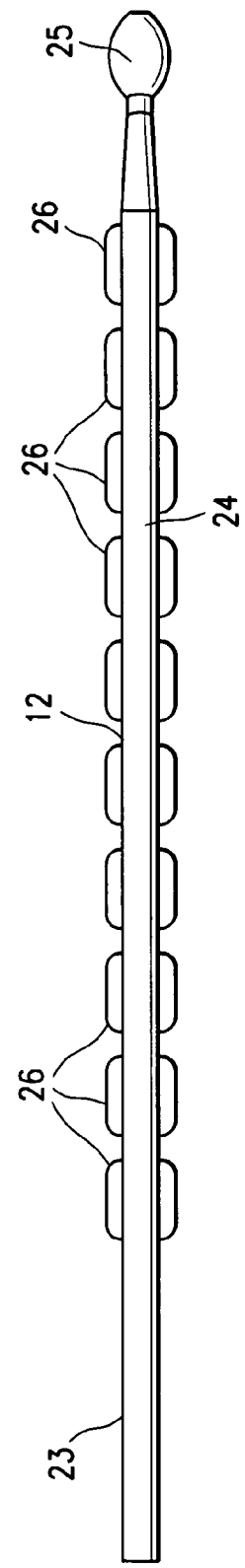
FIG. 2 is an elevational view of the stabilizing member shown in FIG. 1 rotated 90° from that shown in FIG. 1.
Figure 3:
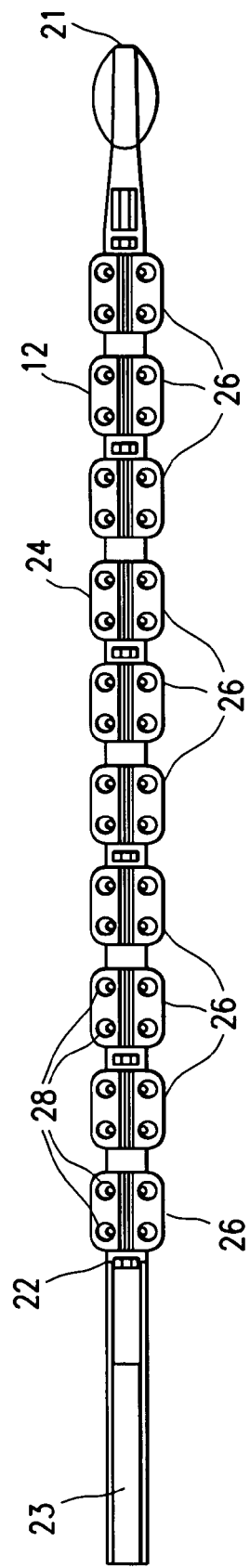
FIG. 3 is an elevational view of the stabilizing member shown in FIG. 1 rotated 180° from that shown in FIG. 2.
Figure 28:
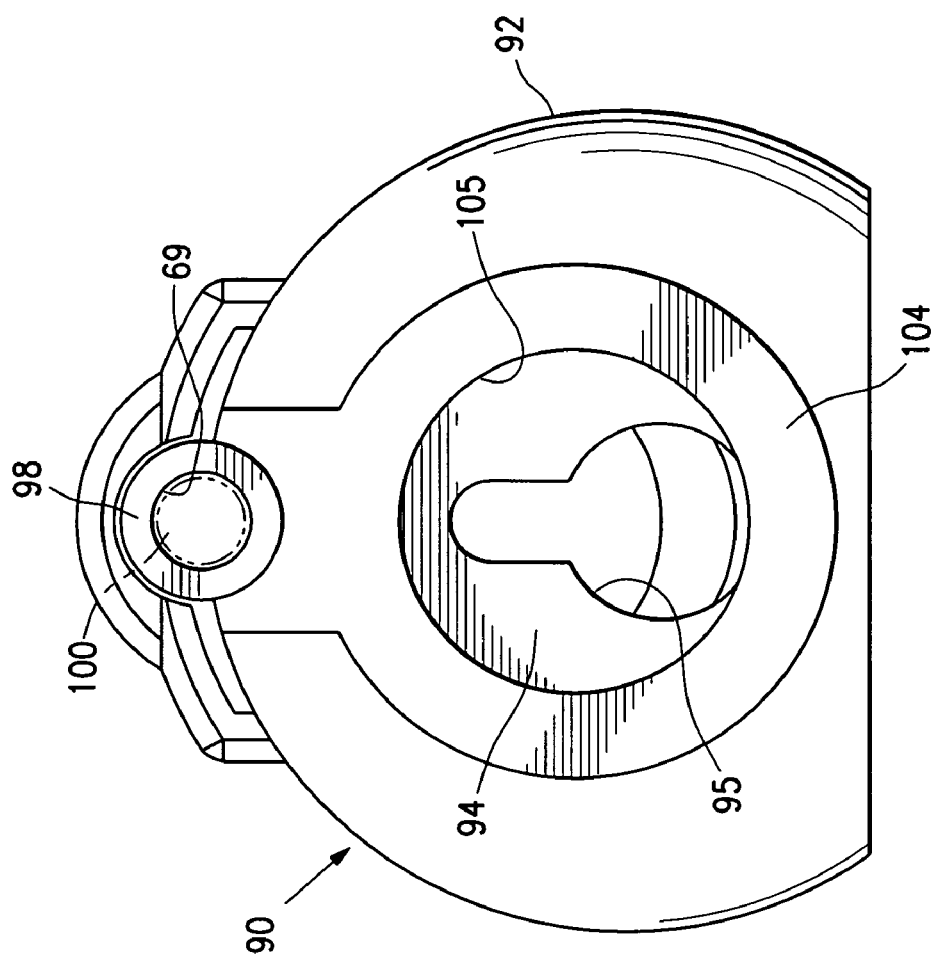
FIG. 28 is an enlarged back view of the stabilizing member shown in FIG. 21.

FIGS. 21-29 illustrate a stabilizing member 90 which is similar in function to the embodiment shown in FIGS. 1-10 and the embodiment shown in FIGS. 11-19. The stabilizer member 90 generally has an elongated body 91 with a plurality of bowed segments 92 and an elongated opening 93 on the underside of the body. Clips 94 (best shown in FIG. 29) are deployed at the smaller ends of the segments 92. The clips 94 have a recess 95 that is configured to receive an electrophysiology (EP) or ablation member (not shown) such as shown in FIG. 1. The clips 94 have recesses 96 and 97 on both sides of the recess 95 to provide fluid communication between adjacent segments 92. As best shown in FIGS. 21A and 28, a first tubular member 98 has a first inner lumen 99 configured to receive a removable elongated stylet or stiffening member 100 and preferably extends to the distal end of the stabilizing member 90. Preferably, the stylet or stiffening member 100 has a shapeable distal end which facilitates guiding the ablation assembly to a desired location. The inner lumen 99 may also be employed for delivery of fluid (e.g. for flushing) to the interior of the individual segments 92 through apertures or ports 101. Alternatively, a separate lumen (not shown) may be provided for fluid delivery. The distal tip 102 of the stabilizing member 90 may be provided with a LED 103 to aid the surgeon or other operating personnel in locating the distal tip of the assembly during the procedure. The stabilizer 90 has a second tubular member 104 with inner lumen 105 which extends to and is in fluid communication with the interior of the stabilizer and opens to the most proximal segment 92. The inner lumen 105 is configured to receive the ablation device or other device which is to be utilized for the procedure. The inner lumen 105 is also employed for applying vacuum to the interior of the stabilizer 90 and the aspiration of fluids therefrom. A separate lumen may be provided for applying a vacuum to the interior.

Vacuum is applied to the interior of the stabilizing member 90 through passageway 105 within proximal shaft section 107 or a separate lumen (not shown) and is maintained throughout the interior of the stabilizing member 90 through openings 96 and 97 of the clips 95. The vacuum will remove fluids from within the interior of the stabilizing member 90 and can aid in securing the stabilizer to an exterior surface of the patient's heart.

In one embodiment, the assembly of stabilizing member 90 and an EP member is advanced through the space between the epicardial and pericardial layers of the patient's heart until the ablation electrodes on the ablation member are deployed in a desirable location. Once the assembly is in an appropriate location vacuum may be applied to the interior of the stabilizer 90 and fluid may be delivered to the interior of the segments 92 through the apertures 103. High frequency electrical energy (RF) may be delivered to the ablation electrodes before, after or during the period when vacuum is applied and/or fluid is delivered to the interior of the stabilizer 90.

A delivery sheath or cannula (not shown) may be utilized to facilitate advancement of the assembly along the posterior side of the patient's heart. The deflectable distal shaft section of the ablation member can be deflected as it exits the distal end of the delivery sheath with the distal end of the sheath supporting the portion of the ablation member extending out the distal end thereof.

The embodiments shown in FIGS. 10-29 allow deployment and manipulation of the assembly from one side of the patient, preferably through a trocar such as schematically shown in FIG. 20. The assembly is advanced around the posterior side of the heart, preferably through a delivery sheath or cannula. The distal end of the delivery sheath is preferably disposed on the right side of the posterior portion of the heart. When the distal portion of the assembly is advanced around the anterior side of the patient's heart, the light on the distal end of the EP member is readily seen by the physician even when disposed between the epicardial and pericardial layers of the patient's heart. The physician may then grasp the distal end of the assembly and place the active portion thereof at the desired location, such as surrounding the patient's pulmonary vein where a continuous lesion is preferably formed to effectively treat atrial fibrillation or flutter and other disorders.

To the extent not already discussed herein, the components of the ablation member can be formed of conventional materials. As previously mentioned, a suitable ablation member 11 or other EP member is the REVELATION T-Flex® available from the present assignee, Cardima, Inc.

The electrical connector 18 on the proximal end of the device may be a commercially available electrical connector such as Part No. PAB-M08-GLA39J or PAB-M08-TLA39J for an eight pin connector or Part No. PAB-M08-GLA39A for a connector with a greater number of pins, e.g. 9-28. The above connectors are available from Lemo USA, Inc. in Santa Rosa, Calif. Suitable connectors for accessory cables connectable to the above connectors include PRB-M08-GLL65J for eight pin connectors and PRB-M08-GII65A for connectors with more than eight pins. The latter connectors are also available from the same source.

While particular forms of the invention have been illustrated and described herein, it will be apparent that various modifications and improvements can be made to the invention. For example, while the various embodiments of the invention have been described herein in terms of stabilizing epicardial tissue, particularly for forming atrial lesions, it should be apparent that the devices and methods of utilizing the device may be employed to stabilize other tissue, e.g. endocardial tissue, and form lesions at other locations. Additionally, the stabilizing member may be employed to stabilize a variety of instruments other than ablation members with respect to a tissue surface, particularly a moving tissue surface such as a beating heart. Moreover, individual features of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention to be defined by the scope of the appended claims as broadly as the prior art will permit.

Terms such a "element", "member", "device", "portion", "component" "section", "assembly", "means", "step" and words of similar import when used herein shall not be construed as invoking the provisions of 35 U.S.C. §112(6) unless the following claims expressly use the term "means" followed by a particular function without specific structure or the term "step" followed by a particular function without specific action. All patents, patent publications and patent applications referred to above are hereby incorporated by reference in their entirety.

What is claimed is:

1. An ablation assembly comprising:
   a. an elongated ablation device having a distal shaft section and at least one ablation electrode on the distal shaft section and;
   b. a stabilizing member which is removably secured to at least the distal shaft section of the ablation device, which has an inner chamber which is configured to receive at least a portion of the ablation device having the at least one electrode, which has at least one opening in a wall thereof in communication with the inner chamber and configured to expose the at least one electrode of the ablation device to facilitate tissue ablation, and which has a plurality of wall segments configured to provide flexibility to at least a portion of the stabilizing member; and
   c. at least one clip formed of material harder than material of the stabilizing member which is secured to the stabilizing member between wall segments and which receives the distal shaft section of the ablation device and facilitates securing the distal shaft section to the stabilizing member.

2. The ablation assembly of claim 1 wherein the stabilizing member is configured to conform to the shape of the distal section of the ablation device.

3. The ablation assembly of claim 1 wherein the stabilizing member has at least one vacuum lumen in fluid communication with the inner chamber.

4. The ablation assembly of claim 1 wherein the stabilizing member has at least one slot within the inner chamber configured to receive at least part of the distal shaft section of the ablation device.

5. The ablation assembly of claim 1 wherein the stabilizing member has at least one fluid delivery lumen extending along a length of the distal shaft section and in fluid communication with the inner chamber.

6. The ablation assembly of claim 1 wherein at least one fluid lumen is in fluid communication with the inner chamber through at least one opening to deliver fluid therethrough to the inner chamber.

7. The ablation assembly of claim 1 wherein the at least one opening of the stabilizing member is configured to engage a tissue surface of the patient's heart.

8. The ablation assembly of claim 7 wherein the tissue engaging opening of the stabilizing member is concave.

9. The ablation assembly of claim 1 wherein the clip is disposed between wall segments.

10. The ablation assembly of claim 9 wherein the wall segments define in part pods.

11. The ablation assembly of claim 10 wherein the stabilizing member has a vacuum lumen extending therein and the pods have vacuum ports in fluid communication with the vacuum lumen.

* * * * *